US009711130B2

(12) United States Patent
Hendrix et al.

(10) Patent No.: US 9,711,130 B2
(45) **Date of Patent: *Jul. 18, 2017**

(54) ADAPTIVE NOISE CANCELING ARCHITECTURE FOR A PERSONAL AUDIO DEVICE

(71) Applicant: Cirrus Logic, Inc., Austin, TX (US)

(72) Inventors: Jon D. Hendrix, Wimberly, TX (US); Gautham Devendra Kamath, Austin, TX (US); Nitin Kwatra, Austin, TX (US); Ali Abdollahzadeh Milani, Austin, TX (US); Jeffrey Alderson, Austin, TX (US)

(73) Assignee: CIRRUS LOGIC, INC., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/130,271

(22) Filed: Apr. 15, 2016

(65) Prior Publication Data

US 2016/0232887 A1 Aug. 11, 2016

Related U.S. Application Data

(63) Continuation of application No. 13/413,920, filed on Mar. 7, 2012, now Pat. No. 9,318,094.

(Continued)

(51) Int. Cl.

*A61F 11/06* (2006.01)
*G10K 11/178* (2006.01)

(Continued)

(52) U.S. Cl.

CPC ........ *G10K 11/178* (2013.01); *G10K 11/1784* (2013.01); *G10K 2210/108* (2013.01);

(Continued)

(58) Field of Classification Search

CPC ......... G10K 11/1784; G10K 2210/108; G10K 2210/3026; G10K 2210/503;

(Continued)

(56) References Cited

U.S. PATENT DOCUMENTS

| | | | |
|---|---|---|---|
| 4,020,567 | A | 5/1977 | Webster |
| 4,649,507 | A | 3/1987 | Inaba et al. |

(Continued)

FOREIGN PATENT DOCUMENTS

| | | | |
|---|---|---|---|
| CN | 101552939 | A | 10/2009 |
| DE | 102011013343 | A1 | 9/2012 |

(Continued)

OTHER PUBLICATIONS

U.S. Appl. No. 15/202,644, filed Jul. 6, 2016, Hendrix, et al.

(Continued)

*Primary Examiner* — Vivian Chin
*Assistant Examiner* — Con P Tran
(74) *Attorney, Agent, or Firm* — Mitch Harris, Atty at Law, LLC; Andrew M. Harris

(57) ABSTRACT

A personal audio device, such as a wireless telephone, includes an adaptive noise canceling (ANC) circuit that adaptively generates an anti-noise signal from a reference microphone signal that measures the ambient audio and an error microphone signal that measures the output of an output transducer plus any ambient audio at that location and injects the anti-noise signal at the transducer output to cause cancellation of ambient audio sounds. A processing circuit uses the reference and error microphone to generate the anti-noise signal, which can be generated by an adaptive filter operating at a multiple of the ANC coefficient update rate. Downlink audio can be combined with the high data rate anti-noise signal by interpolation. High-pass filters in the control paths reduce DC offset in the ANC circuits, and (Continued)

ANC coefficient adaptation can be halted when downlink audio is not detected.

18 Claims, 5 Drawing Sheets

Related U.S. Application Data

(60) Provisional application No. 61/493,162, filed on Jun. 3, 2011.

(51) Int. Cl.
*H04R 3/00* (2006.01)
*H04R 1/10* (2006.01)

(52) U.S. Cl.
CPC ................ *G10K 2210/1081* (2013.01); *G10K 2210/3026* (2013.01); *G10K 2210/3028* (2013.01); *G10K 2210/3051* (2013.01); *G10K 2210/3055* (2013.01); *G10K 2210/30232* (2013.01); *H04R 1/1083* (2013.01); *H04R 3/005* (2013.01)

(58) Field of Classification Search
CPC ..... G10K 2210/305; G10K 2210/3055; G10K 2210/3028; G10K 2210/10; G10K 2210/30232; G10K 11/178; G10K 2210/1081; H04R 1/1083; H04R 3/005
USPC .... 381/71.6, 71.11, 71.2–71.9, 71.12, 71.13, 381/71.14; 704/226; 700/94; 455/570, 455/569.1; 341/123, 122
See application file for complete search history.

(56) References Cited

U.S. PATENT DOCUMENTS

| | | | |
|---|---|---|---|
| 4,926,464 | A | 5/1990 | Schley-May |
| 4,998,241 | A | 3/1991 | Brox et al. |
| 5,018,202 | A | 5/1991 | Takahashi |
| 5,021,753 | A | 6/1991 | Chapman |
| 5,044,373 | A | 9/1991 | Northeved et al. |
| 5,117,401 | A | 5/1992 | Feintuch |
| 5,204,827 | A | 4/1993 | Fujita et al. |
| 5,251,263 | A | 10/1993 | Andrea et al. |
| 5,278,913 | A | 1/1994 | Delfosse et al. |
| 5,321,759 | A | 6/1994 | Yuan |
| 5,337,365 | A | 8/1994 | Hamabe et al. |
| 5,359,662 | A | 10/1994 | Yuan et al. |
| 5,377,276 | A | 12/1994 | Terai et al. |
| 5,386,477 | A | 1/1995 | Popovich et al. |
| 5,410,605 | A | 4/1995 | Sawada et al. |
| 5,425,105 | A | 6/1995 | Lo et al. |
| 5,445,517 | A | 8/1995 | Kondou et al. |
| 5,465,413 | A | 11/1995 | Enge et al. |
| 5,481,615 | A | 1/1996 | Eatwell et al. |
| 5,548,681 | A | 8/1996 | Gleaves et al. |
| 5,550,925 | A | 8/1996 | Hori et al. |
| 5,559,893 | A | 9/1996 | Krokstad et al. |
| 5,563,819 | A | 10/1996 | Nelson |
| 5,586,190 | A | 12/1996 | Trantow et al. |
| 5,633,795 | A | 5/1997 | Popovich |
| 5,640,450 | A | 6/1997 | Watanabe |
| 5,668,747 | A | 9/1997 | Ohashi |
| 5,687,075 | A | 11/1997 | Stothers |
| 5,696,831 | A | 12/1997 | Inanaga et al. |
| 5,699,437 | A | 12/1997 | Finn |
| 5,706,344 | A | 1/1998 | Finn |
| 5,740,256 | A | 4/1998 | Castello Da Costa et al. |
| 5,768,124 | A | 6/1998 | Stothers et al. |
| 5,809,152 | A | 9/1998 | Nakamura et al. |
| 5,815,582 | A | 9/1998 | Claybaugh et al. |
| 5,832,095 | A | 11/1998 | Daniels |
| 5,852,667 | A | 12/1998 | Pan et al. |
| 5,909,498 | A | 6/1999 | Smith |
| 5,940,519 | A | 8/1999 | Kuo |
| 5,946,391 | A | 8/1999 | Dragwidge et al. |
| 5,991,418 | A | 11/1999 | Kuo |
| 6,041,126 | A | 3/2000 | Terai et al. |
| 6,118,878 | A | 9/2000 | Jones |
| 6,181,801 | B1 | 1/2001 | Puthuff et al. |
| 6,185,300 | B1 | 2/2001 | Romesburg |
| 6,219,427 | B1 | 4/2001 | Kates et al. |
| 6,278,786 | B1 | 8/2001 | McIntosh |
| 6,282,176 | B1 | 8/2001 | Hemkumar |
| 6,304,179 | B1 | 10/2001 | Lolito et al. |
| 6,317,501 | B1 | 11/2001 | Matsuo |
| 6,418,228 | B1 | 7/2002 | Terai et al. |
| 6,434,246 | B1 | 8/2002 | Kates et al. |
| 6,434,247 | B1 | 8/2002 | Kates et al. |
| 6,445,799 | B1 | 9/2002 | Taenzer et al. |
| 6,522,746 | B1 | 2/2003 | Marchok et al. |
| 6,542,436 | B1 | 4/2003 | Myllyla |
| 6,650,701 | B1 | 11/2003 | Hsiang et al. |
| 6,683,960 | B1 | 1/2004 | Fujii et al. |
| 6,738,482 | B1 | 5/2004 | Jaber |
| 6,766,292 | B1 | 7/2004 | Chandran |
| 6,768,795 | B2 | 7/2004 | Feltstrom et al. |
| 6,792,107 | B2 | 9/2004 | Tucker et al. |
| 6,850,617 | B1 | 2/2005 | Weigand |
| 6,940,982 | B1 | 9/2005 | Watkins |
| 7,016,504 | B1 | 3/2006 | Shennib |
| 7,034,614 | B2 | 4/2006 | Robinson et al. |
| 7,058,463 | B1 | 6/2006 | Ruha et al. |
| 7,103,188 | B1 | 9/2006 | Jones |
| 7,110,864 | B2 | 9/2006 | Restrepo et al. |
| 7,181,030 | B2 | 2/2007 | Rasmussen et al. |
| 7,321,913 | B2 | 1/2008 | McGrath |
| 7,330,739 | B2 | 2/2008 | Somayajula |
| 7,365,669 | B1 | 4/2008 | Melanson |
| 7,368,918 | B2 | 5/2008 | Henson et al. |
| 7,406,179 | B2 | 7/2008 | Ryan |
| 7,441,173 | B2 | 10/2008 | Restrepo et al. |
| 7,466,838 | B1 | 12/2008 | Mosely |
| 7,555,081 | B2 | 6/2009 | Keele, Jr. |
| 7,680,456 | B2 | 3/2010 | Muhammad et al. |
| 7,742,746 | B2 | 6/2010 | Xiang et al. |
| 7,742,790 | B2 | 6/2010 | Konchitsky et al. |
| 7,817,808 | B2 | 10/2010 | Konchitsky et al. |
| 7,953,231 | B2 | 5/2011 | Ishida |
| 8,019,050 | B2 | 9/2011 | Mactavish et al. |
| 8,085,966 | B2 | 12/2011 | Amsel |
| 8,107,637 | B2 | 1/2012 | Asada et al. |
| 8,135,140 | B2 | 3/2012 | Shridhar et al. |
| 8,144,888 | B2 | 3/2012 | Berkhoff et al. |
| 8,155,334 | B2 | 4/2012 | Joho et al. |
| 8,165,312 | B2 | 4/2012 | Clemow |
| 8,165,313 | B2 | 4/2012 | Carreras |
| 8,218,779 | B2 | 7/2012 | Isberg |
| 8,218,782 | B2 | 7/2012 | Asada et al. |
| D666,169 | S | 8/2012 | Tucker et al. |
| 8,249,262 | B2 | 8/2012 | Chua et al. |
| 8,251,903 | B2 | 8/2012 | LeBoeuf et al. |
| 8,254,589 | B2 | 8/2012 | Mitsuhata |
| 8,290,537 | B2 | 10/2012 | Lee et al. |
| 8,311,243 | B2 | 11/2012 | Tucker et al. |
| 8,315,405 | B2 | 11/2012 | Bakalos et al. |
| 8,325,934 | B2 | 12/2012 | Kuo |
| 8,331,604 | B2 | 12/2012 | Saito et al. |
| 8,374,358 | B2 | 2/2013 | Buck et al. |
| 8,379,884 | B2 | 2/2013 | Horibe et al. |
| 8,401,200 | B2 | 3/2013 | Tiscareno et al. |
| 8,401,204 | B2 | 3/2013 | Odent et al. |
| 8,442,251 | B2 | 5/2013 | Jensen et al. |
| 8,526,627 | B2 | 9/2013 | Asao et al. |
| 8,526,628 | B1 | 9/2013 | Massie et al. |
| 8,532,310 | B2 | 9/2013 | Gauger, Jr. et al. |
| 8,539,012 | B2 | 9/2013 | Clark |
| 8,559,661 | B2 | 10/2013 | Tanghe |
| 8,600,085 | B2 | 12/2013 | Chen et al. |
| 8,737,636 | B2 | 5/2014 | Park et al. |
| 8,775,172 | B2 | 7/2014 | Konchitsky et al. |
| 8,804,974 | B1 | 8/2014 | Melanson |

(56) References Cited

U.S. PATENT DOCUMENTS

| | | | |
|---|---|---|---|
| 8,831,239 | B2 | 9/2014 | Bakalos |
| 8,842,848 | B2 | 9/2014 | Donaldson et al. |
| 8,848,936 | B2 | 9/2014 | Kwatra et al. |
| 8,855,330 | B2 | 10/2014 | Taenzer |
| 8,907,829 | B1 | 12/2014 | Naderi |
| 8,908,877 | B2 | 12/2014 | Abdollahzadeh Milani et al. |
| 8,909,524 | B2 | 12/2014 | Stoltz et al. |
| 8,942,976 | B2 | 1/2015 | Li et al. |
| 8,948,407 | B2 | 2/2015 | Alderson et al. |
| 8,948,410 | B2 | 2/2015 | Van Leest |
| 8,958,571 | B2 | 2/2015 | Kwatra et al. |
| 8,977,545 | B2 | 3/2015 | Zeng et al. |
| 9,020,065 | B2 | 4/2015 | Wyville |
| 9,020,160 | B2 | 4/2015 | Gauger, Jr. |
| 9,031,251 | B2 | 5/2015 | Alcock |
| 9,066,176 | B2 | 6/2015 | Hendrix et al. |
| 9,071,724 | B2 | 6/2015 | Do et al. |
| 9,076,431 | B2 | 7/2015 | Kamath et al. |
| 9,082,391 | B2 | 7/2015 | Yermeche et al. |
| 9,129,586 | B2 | 9/2015 | Bajic et al. |
| 9,202,456 | B2 | 12/2015 | Lee et al. |
| 9,203,366 | B2 | 12/2015 | Eastty |
| 9,478,212 | B1 | 10/2016 | Sorensen et al. |
| 2001/0053228 | A1 | 12/2001 | Jones |
| 2002/0003887 | A1 | 1/2002 | Zhang et al. |
| 2003/0063759 | A1 | 4/2003 | Brennan et al. |
| 2003/0072439 | A1 | 4/2003 | Gupta |
| 2003/0185403 | A1 | 10/2003 | Sibbald |
| 2004/0017921 | A1 | 1/2004 | Mantovani |
| 2004/0047464 | A1 | 3/2004 | Yu et al. |
| 2004/0120535 | A1 | 6/2004 | Woods |
| 2004/0165736 | A1 | 8/2004 | Hetherington et al. |
| 2004/0167777 | A1 | 8/2004 | Hetherington et al. |
| 2004/0202333 | A1 | 10/2004 | Csermak et al. |
| 2004/0240677 | A1 | 12/2004 | Onishi et al. |
| 2004/0242160 | A1 | 12/2004 | Ichikawa et al. |
| 2004/0264706 | A1 | 12/2004 | Ray et al. |
| 2005/0004796 | A1 | 1/2005 | Trump et al. |
| 2005/0018862 | A1 | 1/2005 | Fisher |
| 2005/0117754 | A1 | 6/2005 | Sakawaki |
| 2005/0207585 | A1 | 9/2005 | Christoph |
| 2005/0240401 | A1 | 10/2005 | Ebenezer |
| 2006/0013408 | A1 | 1/2006 | Lee |
| 2006/0018460 | A1 | 1/2006 | McCree |
| 2006/0035593 | A1 | 2/2006 | Leeds |
| 2006/0055910 | A1 | 3/2006 | Lee |
| 2006/0069556 | A1 | 3/2006 | Nadjar et al. |
| 2006/0153400 | A1 | 7/2006 | Fujita et al. |
| 2006/0159282 | A1 | 7/2006 | Borsch |
| 2006/0161428 | A1 | 7/2006 | Fouret |
| 2006/0251266 | A1 | 11/2006 | Saunders et al. |
| 2007/0030989 | A1 | 2/2007 | Kates |
| 2007/0033029 | A1 | 2/2007 | Sakawaki |
| 2007/0038441 | A1 | 2/2007 | Inoue et al. |
| 2007/0047742 | A1 | 3/2007 | Taenzer et al. |
| 2007/0053524 | A1 | 3/2007 | Haulick et al. |
| 2007/0076896 | A1 | 4/2007 | Hosaka et al. |
| 2007/0154031 | A1 | 7/2007 | Avendano et al. |
| 2007/0208520 | A1 | 9/2007 | Zhang et al. |
| 2007/0258597 | A1 | 11/2007 | Rasmussen et al. |
| 2007/0297620 | A1 | 12/2007 | Choy |
| 2008/0019548 | A1 | 1/2008 | Avendano |
| 2008/0101589 | A1 | 5/2008 | Horowitz et al. |
| 2008/0107281 | A1 | 5/2008 | Togami et al. |
| 2008/0144853 | A1 | 6/2008 | Sommerfeldt et al. |
| 2008/0177532 | A1 | 7/2008 | Greiss et al. |
| 2008/0181422 | A1 | 7/2008 | Christoph |
| 2008/0226098 | A1 | 9/2008 | Haulick et al. |
| 2008/0240413 | A1 | 10/2008 | Mohammad et al. |
| 2008/0240455 | A1 | 10/2008 | Inoue et al. |
| 2008/0240457 | A1 | 10/2008 | Inoue et al. |
| 2008/0269926 | A1 | 10/2008 | Xiang et al. |
| 2009/0012783 | A1 | 1/2009 | Klein |
| 2009/0034748 | A1 | 2/2009 | Sibbald |
| 2009/0041260 | A1 | 2/2009 | Jorgensen et al. |
| 2009/0060222 | A1 | 3/2009 | Jeong et al. |
| 2009/0080670 | A1 | 3/2009 | Solbeck et al. |
| 2009/0086990 | A1 | 4/2009 | Christoph |
| 2009/0175461 | A1 | 7/2009 | Nakamura et al. |
| 2009/0175466 | A1 | 7/2009 | Elko et al. |
| 2009/0196429 | A1 | 8/2009 | Ramakrishnan et al. |
| 2009/0220107 | A1 | 9/2009 | Every et al. |
| 2009/0238369 | A1 | 9/2009 | Ramakrishnan et al. |
| 2009/0254340 | A1 | 10/2009 | Sun et al. |
| 2009/0290718 | A1 | 11/2009 | Kahn et al. |
| 2009/0296965 | A1 | 12/2009 | Kojima |
| 2009/0304200 | A1 | 12/2009 | Kim et al. |
| 2009/0311979 | A1 | 12/2009 | Husted et al. |
| 2010/0002891 | A1 | 1/2010 | Shiraishi et al. |
| 2010/0014683 | A1 | 1/2010 | Maeda et al. |
| 2010/0014685 | A1 | 1/2010 | Wurm |
| 2010/0061564 | A1 | 3/2010 | Clemow et al. |
| 2010/0069114 | A1 | 3/2010 | Lee et al. |
| 2010/0082339 | A1 | 4/2010 | Konchitsky et al. |
| 2010/0098263 | A1 | 4/2010 | Pan et al. |
| 2010/0098265 | A1 | 4/2010 | Pan et al. |
| 2010/0124335 | A1 | 5/2010 | Wessling et al. |
| 2010/0124337 | A1 | 5/2010 | Wertz et al. |
| 2010/0131269 | A1 | 5/2010 | Park et al. |
| 2010/0142715 | A1 | 6/2010 | Goldstein et al. |
| 2010/0150367 | A1 | 6/2010 | Mizuno |
| 2010/0158330 | A1 | 6/2010 | Guissin et al. |
| 2010/0166203 | A1 | 7/2010 | Peissig et al. |
| 2010/0166206 | A1 | 7/2010 | Macours |
| 2010/0195838 | A1 | 8/2010 | Bright |
| 2010/0195844 | A1 | 8/2010 | Christoph et al. |
| 2010/0207317 | A1 | 8/2010 | Iwami et al. |
| 2010/0226210 | A1 | 9/2010 | Kordis et al. |
| 2010/0239126 | A1 | 9/2010 | Grafenberg et al. |
| 2010/0246855 | A1 | 9/2010 | Chen |
| 2010/0260345 | A1 | 10/2010 | Shridhar et al. |
| 2010/0266137 | A1 | 10/2010 | Sibbald et al. |
| 2010/0272276 | A1 | 10/2010 | Carreras et al. |
| 2010/0272283 | A1 | 10/2010 | Carreras et al. |
| 2010/0284546 | A1 | 11/2010 | DeBrunner et al. |
| 2010/0291891 | A1 | 11/2010 | Ridgers et al. |
| 2010/0296666 | A1 | 11/2010 | Lin |
| 2010/0310086 | A1 | 12/2010 | Magrath et al. |
| 2011/0026724 | A1 | 2/2011 | Doclo |
| 2011/0091047 | A1 | 4/2011 | Konchitsky et al. |
| 2011/0099010 | A1 | 4/2011 | Zhang |
| 2011/0106533 | A1 | 5/2011 | Yu |
| 2011/0116654 | A1 | 5/2011 | Chan et al. |
| 2011/0129098 | A1 | 6/2011 | Delano et al. |
| 2011/0130176 | A1 | 6/2011 | Magrath et al. |
| 2011/0142247 | A1 | 6/2011 | Fellers et al. |
| 2011/0144984 | A1 | 6/2011 | Konchitsky |
| 2011/0158419 | A1 | 6/2011 | Theverapperuma et al. |
| 2011/0206214 | A1 | 8/2011 | Christoph et al. |
| 2011/0288860 | A1 | 11/2011 | Schevciw et al. |
| 2011/0293103 | A1 | 12/2011 | Park et al. |
| 2011/0299695 | A1 | 12/2011 | Nicholson |
| 2011/0305347 | A1 | 12/2011 | Wurm |
| 2011/0317848 | A1 | 12/2011 | Ivanov et al. |
| 2012/0135787 | A1 | 5/2012 | Kusunoki et al. |
| 2012/0140917 | A1 | 6/2012 | Nicholson et al. |
| 2012/0140942 | A1 | 6/2012 | Loeda |
| 2012/0140943 | A1 | 6/2012 | Hendrix et al. |
| 2012/0148062 | A1 | 6/2012 | Scarlett et al. |
| 2012/0155666 | A1 | 6/2012 | Nair |
| 2012/0170766 | A1 | 7/2012 | Alves et al. |
| 2012/0179458 | A1 | 7/2012 | Oh et al. |
| 2012/0215519 | A1 | 8/2012 | Park et al. |
| 2012/0250873 | A1 | 10/2012 | Bakalos et al. |
| 2012/0259626 | A1 | 10/2012 | Li et al. |
| 2012/0263317 | A1 | 10/2012 | Shin et al. |
| 2012/0281850 | A1 | 11/2012 | Hyatt |
| 2012/0300955 | A1 | 11/2012 | Iseki et al. |
| 2012/0300958 | A1 | 11/2012 | Klemmensen |
| 2012/0300960 | A1 | 11/2012 | Mackay et al. |
| 2012/0308025 | A1 | 12/2012 | Hendrix et al. |
| 2012/0308027 | A1 | 12/2012 | Kwatra |
| 2012/0308028 | A1 | 12/2012 | Kwatra et al. |
| 2013/0010982 | A1 | 1/2013 | Elko et al. |

(56) References Cited

U.S. PATENT DOCUMENTS

| | | | |
|---|---|---|---|
| 2013/0083939 | A1 | 4/2013 | Fellers et al. |
| 2013/0156238 | A1 | 6/2013 | Birch et al. |
| 2013/0195282 | A1 | 8/2013 | Ohita et al. |
| 2013/0243198 | A1 | 9/2013 | Van Rumpt |
| 2013/0243225 | A1 | 9/2013 | Yokota |
| 2013/0272539 | A1 | 10/2013 | Kim et al. |
| 2013/0287218 | A1 | 10/2013 | Alderson et al. |
| 2013/0287219 | A1 | 10/2013 | Hendrix et al. |
| 2013/0301842 | A1 | 11/2013 | Hendrix et al. |
| 2013/0301846 | A1 | 11/2013 | Alderson et al. |
| 2013/0301847 | A1 | 11/2013 | Alderson et al. |
| 2013/0301848 | A1 | 11/2013 | Zhou et al. |
| 2013/0301849 | A1 | 11/2013 | Alderson et al. |
| 2013/0315403 | A1 | 11/2013 | Samuelsson |
| 2013/0343556 | A1 | 12/2013 | Bright |
| 2013/0343571 | A1 | 12/2013 | Rayala et al. |
| 2014/0016803 | A1 | 1/2014 | Puskarich |
| 2014/0036127 | A1 | 2/2014 | Pong et al. |
| 2014/0044275 | A1 | 2/2014 | Goldstein et al. |
| 2014/0050332 | A1 | 2/2014 | Nielsen et al. |
| 2014/0072134 | A1 | 3/2014 | Po et al. |
| 2014/0086425 | A1 | 3/2014 | Jensen et al. |
| 2014/0146976 | A1 | 5/2014 | Rundle |
| 2014/0169579 | A1 | 6/2014 | Azmi |
| 2014/0177851 | A1 | 6/2014 | Kitazawa et al. |
| 2014/0177890 | A1 | 6/2014 | Hojlund et al. |
| 2014/0211953 | A1 | 7/2014 | Alderson et al. |
| 2014/0270222 | A1 | 9/2014 | Hendrix et al. |
| 2014/0270223 | A1 | 9/2014 | Li et al. |
| 2014/0270224 | A1 | 9/2014 | Zhou et al. |
| 2014/0294182 | A1 | 10/2014 | Axelsson et al. |
| 2014/0307887 | A1 | 10/2014 | Alderson |
| 2014/0307888 | A1 | 10/2014 | Alderson et al. |
| 2014/0307890 | A1 | 10/2014 | Zhou et al. |
| 2014/0314244 | A1 | 10/2014 | Yong |
| 2014/0314247 | A1 | 10/2014 | Zhang |
| 2014/0341388 | A1 | 11/2014 | Goldstein |
| 2014/0369517 | A1 | 12/2014 | Zhou et al. |
| 2015/0092953 | A1 | 4/2015 | Abdollahzadeh Milani et al. |
| 2015/0104032 | A1 | 4/2015 | Kwatra et al. |
| 2015/0161981 | A1 | 6/2015 | Kwatra |
| 2015/0195646 | A1 | 7/2015 | Kumar et al. |
| 2015/0256953 | A1 | 9/2015 | Kwatra et al. |
| 2015/0365761 | A1 | 12/2015 | Alderson et al. |
| 2016/0063988 | A1 | 3/2016 | Hendrix et al. |

FOREIGN PATENT DOCUMENTS

| | | | |
|---|---|---|---|
| EP | 0412902 | A2 | 2/1991 |
| EP | 0756407 | A2 | 1/1997 |
| EP | 0898266 | A2 | 2/1999 |
| EP | 1691577 | A2 | 8/2006 |
| EP | 1880699 | A2 | 1/2008 |
| EP | 1921603 | A2 | 5/2008 |
| EP | 1947642 | A1 | 7/2008 |
| EP | 2133866 | A1 | 12/2009 |
| EP | 2216774 | A1 | 8/2010 |
| EP | 2237573 | A1 | 10/2010 |
| EP | 2259250 | A1 | 12/2010 |
| EP | 2395500 | A1 | 12/2011 |
| EP | 2395501 | A1 | 12/2011 |
| EP | 2551845 | A1 | 1/2013 |
| GB | 2401744 | A | 11/2004 |
| GB | 2436657 | A | 10/2007 |
| GB | 2455821 | A | 6/2009 |
| GB | 2455824 | A | 6/2009 |
| GB | 2455828 | A | 6/2009 |
| GB | 2484722 | A | 4/2012 |
| GB | 2539280 | A | 12/2016 |
| JP | H05265468 | | 10/1993 |
| JP | 06006246 | | 1/1994 |
| JP | H06-186985 | A | 7/1994 |
| JP | H06232755 | | 8/1994 |
| JP | 07098592 | | 4/1995 |
| JP | 07104769 | | 4/1995 |
| JP | 07240989 | | 9/1995 |
| JP | 07325588 | | 12/1995 |
| JP | H07334169 | | 12/1995 |
| JP | H08227322 | | 9/1996 |
| JP | H10247088 | | 9/1998 |
| JP | H10257159 | | 9/1998 |
| JP | H11305783 | A | 11/1999 |
| JP | 2000089770 | | 3/2000 |
| JP | 2002010355 | | 1/2002 |
| JP | 2004007107 | | 1/2004 |
| JP | 2006217542 | A | 8/2006 |
| JP | 2007060644 | | 3/2007 |
| JP | 2008015046 | A | 1/2008 |
| JP | 2010277025 | | 12/2010 |
| JP | 2011055494 | | 3/2011 |
| JP | 2011061449 | | 3/2011 |
| WO | WO 9113429 | | 9/1991 |
| WO | WO 9304529 | | 3/1993 |
| WO | WO 9407212 | | 3/1994 |
| WO | WO 9911045 | | 3/1999 |
| WO | WO 03015074 | A1 | 2/2003 |
| WO | WO 03015275 | A1 | 2/2003 |
| WO | WO 2004009007 | A1 | 1/2004 |
| WO | WO 2004017303 | A1 | 2/2004 |
| WO | WO 2006125061 | A1 | 11/2006 |
| WO | WO 2006128768 | A1 | 12/2006 |
| WO | WO 2007007916 | A1 | 1/2007 |
| WO | WO 2007011337 | | 1/2007 |
| WO | WO 2007110807 | A2 | 10/2007 |
| WO | WO 2007113487 | A1 | 11/2007 |
| WO | WO 2009041012 | A1 | 4/2009 |
| WO | WO 2009110087 | A1 | 9/2009 |
| WO | WO 2009155696 | A1 | 12/2009 |
| WO | WO 2010117714 | A1 | 10/2010 |
| WO | WO 2010131154 | A1 | 11/2010 |
| WO | WO 2012134874 | A1 | 10/2012 |
| WO | WO-2013106370 | A1 | 7/2013 |
| WO | WO 2015038255 | A1 | 3/2015 |
| WO | WO 2015088639 | A1 | 6/2015 |
| WO | WO 2015088651 | A1 | 6/2015 |
| WO | WO 2016054186 | A1 | 4/2016 |
| WO | WO-2016100602 | A1 | 6/2016 |

OTHER PUBLICATIONS

U.S. Appl. No. 14/832,585, filed Aug. 21, 2015, Zhou.

U.S. Appl. No. 15/241,375, filed Aug. 19, 2016, Lu, et al.

U.S. Appl. No. 15/070,564, filed Mar. 15, 2016, Zhou, et al.

Wu, et al., "Decoupling feedforward and feedback structures in hybrid active noise control systems for uncorrelated narrowband disturbances", Journal of Sound and Vibration, vol. 350, Aug. 18, 2015, pp. 1-10, Elsevier.

Lopez-Caudana, et al., "A Hybrid Noise Cancelling Algorithm with Secondary Path Estimation", WSEAS Transactions on Signal Processing, vol. 4, No. 12, Dec. 2008, pp. 677-687, Mexico.

U.S. Appl. No. 13/686,353, filed Nov. 27, 2012, Hendrix, et al.

U.S. Appl. No. 13/794,931, filed Mar. 12, 2013, Lu, et al.

U.S. Appl. No. 13/794,979, filed Mar. 12, 2013, Alderson, et al.

U.S. Appl. No. 14/197,814, filed Mar. 5, 2014, Kaller, et al.

U.S. Appl. No. 14/210,537, filed Mar. 14, 2014, Abdollahzadeh Milani, et al.

U.S. Appl. No. 14/210,589, filed Mar. 14, 2014, Abdollahzadeh Milani, et al.

U.S. Appl. No. 13/762,504, filed Feb. 8, 2013, Abdollahzadeh Milani, et al.

U.S. Appl. No. 13/721,832, filed Dec. 20, 2012, Lu, et al.

U.S. Appl. No. 13/724,656, filed Dec. 21, 2012, Lu, et al.

U.S. Appl. No. 14/252,235, filed Apr. 14, 2014, Lu, et al.

U.S. Appl. No. 13/968,013, filed Aug. 15, 2013, Abdollahzadeh Milani, et al.

U.S. Appl. No. 13/924,935, filed Jun. 24, 2013, Hellman.

U.S. Appl. No. 14/101,955, filed Dec. 10, 2013, Alderson.

U.S. Appl. No. 14/101,777, filed Dec. 10, 2013, Alderson et al.

U.S. Appl. No. 14/656,124, filed Mar. 12, 2015, Hendrix, et al.

U.S. Appl. No. 14/734,321, filed Jun. 9, 2015, Alderson, et al.

(56) References Cited

OTHER PUBLICATIONS

Lane, et al., "Voice Level: Autophonic Scale, Perceived Loudness, and the Effects of Sidetone", The Journal of the Acoustical Society of America, Feb. 1961, pp. 160-167, vol. 33, No. 2., Cambridge, MA, US.
Liu, et al., "Compensatory Responses to Loudness-shifted Voice Feedback During Production of Mandarin Speech", Journal of the Acoustical Society of America, Oct. 2007, pp. 2405-2412, vol. 122, No. 4.
Paepcke, et al., "Yelling in the Hall: Using Sidetone to Address a Problem with Mobile Remote Presence Systems", Symposium on User Interface Software and Technology, Oct. 16-19, 2011, 10 pages (pp. 1-10 in pdf), Santa Barbara, CA, US.
Therrien, et al., "Sensory Attenuation of Self-Produced Feedback: The Lombard Effect Revisited", PLOS ONE, Nov. 2012, pp. 1-7, vol. 7, Issue 11, e49370, Ontario, Canada.
Abdollahzadeh Milani, et al., "On Maximum Achievable Noise Reduction in ANC Systems",2010 IEEE International Conference on Acoustics Speech and Signal Processing, Mar. 14-19, 2010, pp. 349-352, Dallas, TX, US.
Cohen, Israel, "Noise Spectrum Estimation in Adverse Environments: Improved Minima Controlled Recursive Averaging", IEEE Transactions on Speech and Audio Processing, Sep. 2003, pp. 1-11, vol. 11, Issue 5, Piscataway, NJ, US.
Ryan, et al., "Optimum Near-Field Performance of Microphone Arrays Subject to a Far-Field Beampattern Constraint", J. Acoust. Soc. Am., Nov. 2000, pp. 2248-2255, 108 (5), Pt. 1, Ottawa, Ontario, Canada.
Cohen, et al., "Noise Estimation by Minima Controlled Recursive Averaging for Robust Speech Enhancement", IEEE Signal Processing Letters, Jan. 2002, pp. 12-15, vol. 9, No. 1, Piscataway, NJ, US.
Martin, Rainer, "Noise Power Spectral Density Estimation Based on Optimal Smoothing and Minimum Statistics", IEEE Transactions on Speech and Audio Processing, Jul. 2001, pp. 504-512, vol. 9, No. 5, Piscataway, NJ, US.
Martin, Rainer, "Spectral Subtraction Based on Minimum Statistics", Signal Processing VII Theories and Applications, Proceedings of EUSIPCO-94, 7th European Signal Processing Conference, Sep. 13-16, 1994, pp. 1182-1185, vol. III, Edinburgh, Scotland, U.K.
Booij, et al., "Virtual sensors for local, three dimensional, broadband multiple-channel active noise control and the effects on the quiet zones", Proceedings of the International Conference on Noise and Vibration Engineering, ISMA 2010, Sep. 20-22, 2010, pp. 151-166, Leuven.
Kuo, et al., "Residual noise shaping technique for active noise control systems", J. Acoust. Soc. Am. 95 (3), Mar. 1994, pp. 1665-1668.
Lopez-Gaudana, Edgar Omar, "Active Noise Cancellation: The Unwanted Signal and the Hybrid Solution", Adaptive Filtering Applications, Dr. Lino Garcia (Ed.), Jul. 2011, pp. 49-84, ISBN: 978-953-307-306-4, InTech.
Senderowicz, et al., "Low-Voltage Double-Sampled Delta-Sigma Converters", IEEE Journal on Solid-State Circuits, Dec. 1997, pp. 1907-1919, vol. 32, No. 12, Piscataway, NJ.
Hurst, et al., "An improved double sampling scheme for switched-capacitor delta-sigma modulators", 1992 IEEE Int. Symp. on Circuits and Systems, May 10-13, 1992, vol. 3, pp. 1179-1182, San Diego, CA.
Campbell, Mikey, "Apple looking into self-adjusting earbud headphones with noise cancellation tech", Apple Insider, Jul. 4, 2013, pp. 1-10 (10 pages in pdf), downloaded on May 14, 2014 from http://appleinsider.com/articles/13/07/04/apple-looking-into-self-adjusting-earbud-headphones-with-noise-cancellation-tech.
Jin, et al. "A simultaneous equation method-based online secondary path modeling algorithm for active noise control", Journal of Sound and Vibration, Apr. 25, 2007, pp. 455-474, vol. 303, No. 3-5, London, GB.
Erkelens, et al., "Tracking of Nonstationary Noise Based on Data-Driven Recursive Noise Power Estimation", IEEE Transactions on Audio Speech and Language Processing, Aug. 2008, pp. 1112-1123, vol. 16, No. 6, Piscataway, NJ, US.
Rao, et al., "A Novel Two State Single Channel Speech Enhancement Technique", India Conference (INDICON) 2011 Annual IEEE, IEEE, Dec. 2011, 6 pages (pp. 1-6 in pdf), Piscataway, NJ, US.
Rangachari, et al., "A noise-estimation algorithm for highly non-stationary environments", Speech Communication, Feb. 2006, pp. 220-231, vol. 48, No. 2. Elsevier Science Publishers.
Parkins, et al., "Narrowband and broadband active control in an enclosure using the acoustic energy density", J. Acoust. Soc. Am. Jul. 2000, pp. 192-203, vol. 108, issue 1, US.
Feng, Jinwei et al., "A broadband self-tuning active noise equaliser", Signal Processing, Elsevier Science Publishers B.V. Amsterdam, NL, vol. 62, No. 2, Oct. 1, 1997, pp. 251-256.
Zhang, Ming et al., "A Robust Online Secondary Path Modeling Method with Auxiliary Noise Power Scheduling Strategy and Norm Constraint Manipulation", IEEE Transactions on Speech and Audio Processing, IEEE Service Center, New York, NY, vol. 11, No. 1, Jan. 1, 2003.
Lopez-Gaudana, Edgar et al., "A hybrid active noise cancelling with secondary path modeling", 51st Midwest Symposium on Circuits and Systems, 2008, MWSCAS 2008, Aug. 10, 2008, pp. 277-280.
Widrow, B., et al., Adaptive Noice Cancelling; Principles and Applications, Proceedings of the IEEE, Dec. 1975, pp. 1692-1716, vol. 63, No. 13, IEEE, New York, NY, US.
Morgan, et al., A Delayless Subband Adaptive Filter Architecture, IEEE Transactions on Signal Processing, IEEE Service Center, Aug. 1995, pp. 1819-1829, vol. 43, No. 8, New York, NY, US.
Rafaely, Boaz, "Active Noise Reducing Headset—an Overview", The 2001 International Congress and Exhibition on Noice Control Engineering, Aug. 27-30, 2001, 10 pages (pp. 1-10 in pdf), The Netherlands.
Ray, et al., "Hybrid Feedforward-Feedback Active Noise Reduction for Hearing Protection and Communication", The Journal of the Acoustical Society of America, American Institute of Physics for the Acoustical Society of America, Jan. 2006, pp. 2026-2036, vol. 120, No. 4, New York, NY.
Office Action in U.S. Appl. No. 13/413,920 mailed on Aug. 28, 2014, 35 pages (pp. 1-35 in pdf).
Final Office Action in U.S. Appl. No. 13/413,920 mailed on Jul. 7, 2015, 35 pages (pp. 1-35 in pdf).
Notice of Allowance in U.S. Appl. No. 13/413,920 mailed on Oct. 23, 2015, 36 pages (pp. 1-36 in pdf).
Notice of Allowance in U.S. Appl. No. 13/413,920 mailed on Feb. 29, 2016, 26 pages (pp. 1-11 in pdf).
International Search Report and Written Opinion in PCT/US2012/035815 mailed on Jul. 25, 2013, 22 pages (pp. 1-22 in pdf).
Written Opinion of the International Preliminary Examining Authority in PCT/US2012/035815 mailed on Feb. 26, 2014, 22 pages (pp. 1-11 in pdf).
International Preliminary Report on Patentability in PCT/US2012/035815 mailed on May 14, 2014, 44 pages (pp. 1-44 in pdf).
Goeckler, H.G. et al., "Efficient Multirate Digital Filters Based on Fractional Polyphase Decomposition for Subnyquist Processing", Proceedings of the European Conference on Circuit Theory & Design, vol. 1, Jan. 1, 1999, pp. 409-412.
Pfann, et al., "LMS Adaptive Filtering with Delta-Sigma Modulated Input Signals," IEEE Signal Processing Letters, Apr. 1998, pp. 95-97, vol. 5, No. 4, IEEE Press, Piscataway, NJ.
Toochinda, et al. "A Single-Input Two-Output Feedback Formulation for ANC Problems," Proceedings of the 2001 American Control Conference, Jun. 2001, pp. 923-928, vol. 2, Arlington, VA.
Kuo, et al., "Active Noise Control: A Tutorial Review," Proceedings of the IEEE, Jun. 1999, pp. 943-973, vol. 87, No. 6, IEEE Press, Piscataway, NJ.
Johns, et al., "Continuous-Time LMS Adaptive Recursive Filters," IEEE Transactions on Circuits and Systems, Jul. 1991, pp. 769-778, vol. 38, No. 7, IEEE Press, Piscataway, NJ.
Shoval, et al., "Comparison of Dc Offset Effects in Four LMS Adaptive Algorithms," IEEE Transactions on Circuits and Systems II: Analog and Digital Processing, Mar. 1995, pp. 176-185, vol. 42, Issue 3, IEEE Press, Piscataway, NJ.

(56) References Cited

OTHER PUBLICATIONS

Mali, Dilip, "Comparison of DC Offset Effects on LMS Algorithm and its Derivatives," International Journal of Recent Trends in Engineering, May 2009, pp. 323-328, vol. 1, No. 1, Academy Publisher.
Kates, James M., "Principles of Digital Dynamic Range Compression," Trends in Amplification, Spring 2005, pp. 45-76, vol. 9, No. 2, Sage Publications.
Gao, et al., "Adaptive Linearization of a Loudspeaker," IEEE International Conference on Acoustics, Speech, and Signal Processing, Apr. 14-17, 1991, pp. 3589-3592, Toronto, Ontario, CA.
Silva, et al., "Convex Combination of Adaptive Filters With Different Tracking Capabilities," IEEE International Conference on Acoustics, Speech, and Signal Processing, Apr. 15-20, 2007, pp. III 925-928, vol. 3, Honolulu, HI, USA.
Akhtar, et al., "A Method for Online Secondary Path Modeling in Active Noise Control Systems," IEEE International Symposium on Circuits and Systems, May 23-26, 2005, pp. 264-267, vol. 1, Kobe, Japan.
Davari, et al., "A New Online Secondary Path Modeling Method for Feedforward Active Noise Control Systems," IEEE International Conference on Industrial Technology, Apr. 21-24, 2008, pp. 1-6, Chengdu, China.
Lan, et al., "An Active Noise Control System Using Online Secondary Path Modeling With Reduced Auxiliary Noise," IEEE Signal Processing Letters, Jan. 2002, pp. 16-18, vol. 9, Issue 1, IEEE Press, Piscataway, NJ.
Liu, et al., "Analysis of Online Secondary Path Modeling With Auxiliary Noise Scaled by Residual Noise Signal," IEEE Transactions on Audio, Speech and Language Processing, Nov. 2010, pp. 1978-1993, vol. 18, Issue 8, IEEE Press, Piscataway, NJ.
Black, John W., "An Application of Side-Tone in Subjective Tests of Microphones and Headsets", Project Report No. NM 001 064. 01.20, Research Report of the U.S. Naval School of Aviation Medicine, Feb. 1, 1954, 12 pages (pp. 1-12 in pdf), Pensacola, FL, US.
Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-13 in pdf), Pensacola, FL, US.

ADAPTIVE NOISE CANCELING ARCHITECTURE FOR A PERSONAL AUDIO DEVICE

This U.S. Patent Application is a Continuation of and claims priority under 35 U.S.C. §120 to U.S. patent application Ser. No. 13/413,920, filed on Mar. 7, 2012 published as U.S. Patent Publication No. 20120308025 on Dec. 6, 2012. This U.S. Patent Application also claims priority thereby to U.S. Provisional Patent Application Ser. No. 61/493,162 filed on Jun. 3, 2011.

BACKGROUND OF THE INVENTION

1. Field of the Invention

The present invention relates generally to personal audio devices such as wireless telephones that include adaptive noise cancellation (ANC), and more specifically, to architectural features of an ANC system integrated in a personal audio device.

2. Background of the Invention

Wireless telephones, such as mobile/cellular telephones, cordless telephones, and other consumer audio devices, such as mp3 players, are in widespread use. Performance of such devices with respect to intelligibility can be improved by providing noise canceling using a microphone to measure ambient acoustic events and then using signal processing to insert an anti-noise signal into the output of the device to cancel the ambient acoustic events.

Since the acoustic environment around personal audio devices such as wireless telephones can change dramatically, depending on the sources of noise that are present and the position of the device itself, it is desirable to adapt the noise canceling to take into account such environmental changes. However, adaptive noise canceling circuits can be complex, consume additional power, and can generate undesirable results under certain circumstances.

Therefore, it would be desirable to provide a personal audio device, including a wireless telephone, that provides noise cancellation that is effective, energy efficient, and/or has less complexity.

SUMMARY OF THE INVENTION

The above stated objectives of providing a personal audio device providing effective noise cancellation with lower power consumption and/or lower complexity, is accomplished in a personal audio device, a method of operation, and an integrated circuit.

The personal audio device includes a housing, with a transducer mounted on the housing for reproducing an audio signal that includes both source audio for playback to a listener and an anti-noise signal for countering the effects of ambient audio sounds in an acoustic output of the transducer, which may include the integrated circuit to provide adaptive noise-canceling (ANC) functionality. The method is a method of operation of the personal audio device and integrated circuit. A reference microphone is mounted on the housing to provide a reference microphone signal indicative of the ambient audio sounds. An error microphone is included for controlling the adaptation of the anti-noise signal to cancel the ambient audio sounds and for correcting for the electro-acoustic path from the output of the processing circuit through the environment of the transducer. The personal audio device further includes an ANC processing circuit within the housing for adaptively generating an anti-noise signal from the reference microphone signal and reference microphone using one or more adaptive filters, such that the anti-noise signal causes substantial cancellation of the ambient audio sounds.

The ANC circuit implements an adaptive filter that generates the anti-noise signal that may be operated at a multiple of the ANC coefficient update rate. Sigma-delta modulators can be included in the higher sample rate signal path(s) to reduce the width of the adaptive filter(s) and other processing blocks. High-pass filters in the control paths may be included to reduce DC offset in the ANC circuits, and ANC adaptation can be halted when downlink audio is absent. When downlink audio is present, it can be combined with the high data rate anti-noise signal by interpolation and ANC adaptation is resumed.

The foregoing and other objectives, features, and advantages of the invention will be apparent from the following, more particular, description of the preferred embodiment of the invention, as illustrated in the accompanying drawings.

DESCRIPTION OF ILLUSTRATIVE EMBODIMENT

The present invention encompasses noise canceling techniques and circuits that can be implemented in a personal audio device, such as a wireless telephone. The personal audio device includes an adaptive noise canceling (ANC) circuit that measures the ambient acoustic environment and generates a signal that is injected in the speaker (or other transducer) output to cancel ambient acoustic events. A reference microphone is provided to measure the ambient acoustic environment and an error microphone is included for controlling the adaptation of the anti-noise signal to cancel the ambient audio sounds and for correcting for the electro-acoustic path from the output of the processing circuit through the transducer. The coefficient control of the adaptive filter that generates the anti-noise signal may be operated at a baseband rate much lower than a sample rate of the adaptive filter, reducing power consumption and complexity of the ANC processing circuits. High-pass filters can be included in the feedback paths that provide the inputs to the coefficient control, to reduce DC offset in the ANC control loop, and the ANC adaptation may be halted when downlink audio is absent, so that adaptation of the adaptive filter does not proceed under conditions that might lead to instability. When downlink audio, which may be provided at baseband and combined with the higher-data rate audio by interpolation, is detected, adaptation of the adaptive filter coefficients is resumed.

Figure 1:
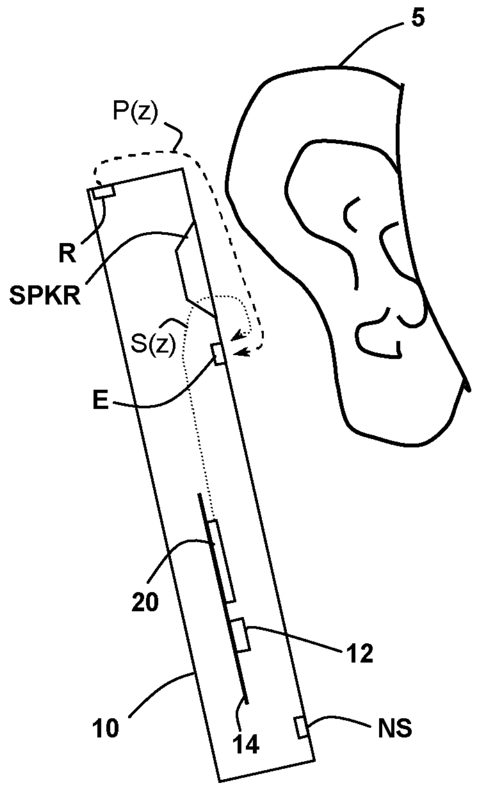
FIG. 1 is an illustration of a wireless telephone 10 in accordance with an embodiment of the present invention.

Referring now to FIG. 1, a wireless telephone 10 is illustrated in accordance with an embodiment of the present invention is shown in proximity to a human ear 5. Illustrated wireless telephone 10 is an example of a device in which techniques in accordance with embodiments of the invention may be employed, but it is understood that not all of the elements or configurations embodied in illustrated wireless telephone 10, or in the circuits depicted in subsequent illustrations, are required in order to practice the invention recited in the Claims. Wireless telephone 10 includes a transducer such as speaker SPKR that reproduces distant speech received by wireless telephone 10, along with other local audio event such as ringtones, stored audio program material, injection of near-end speech (i.e., the speech of the user of wireless telephone 10) to provide a balanced conversational perception, and other audio that requires reproduction by wireless telephone 10, such as sources from web-pages or other network communications received by wireless telephone 10 and audio indications such as battery low and other system event notifications. A near-speech microphone NS is provided to capture near-end speech, which is transmitted from wireless telephone 10 to the other conversation participant(s).

Wireless telephone 10 includes adaptive noise canceling (ANC) circuits and features that inject an anti-noise signal into speaker SPKR to improve intelligibility of the distant speech and other audio reproduced by speaker SPKR. A reference microphone R is provided for measuring the ambient acoustic environment, and is positioned away from the typical position of a user's mouth, so that the near-end speech is minimized in the signal produced by reference microphone R. A third microphone, error microphone E is provided in order to further improve the ANC operation by providing a measure of the ambient audio combined with the audio reproduced by speaker SPKR close to ear 5, when wireless telephone 10 is in close proximity to ear 5. Exemplary circuit 14 within wireless telephone 10 includes an audio CODEC integrated circuit 20 that receives the signals from reference microphone R, near speech microphone NS and error microphone E and interfaces with other integrated circuits such as an RF integrated circuit 12 containing the wireless telephone transceiver. In other embodiments of the invention, the circuits and techniques disclosed herein may be incorporated in a single integrated circuit that contains control circuits and other functionality for implementing the entirety of the personal audio device, such as an MP3 player-on-a-chip integrated circuit.

In general, the ANC techniques of the present invention measure ambient acoustic events (as opposed to the output of speaker SPKR and/or the near-end speech) impinging on reference microphone R, and by also measuring the same ambient acoustic events impinging on error microphone E, the ANC processing circuits of illustrated wireless telephone 10 adapt an anti-noise signal generated from the output of reference microphone R to have a characteristic that minimizes the amplitude of the ambient acoustic events at error microphone E. Since acoustic path P(z) extends from reference microphone R to error microphone E, the ANC circuits are essentially estimating acoustic path P(z) combined with removing effects of an electro-acoustic path S(z) that represents the response of the audio output circuits of CODEC IC 20 and the acoustic/electric transfer function of speaker SPKR including the coupling between speaker SPKR and error microphone E in the particular acoustic environment, which is affected by the proximity and structure of ear 5 and other physical objects and human head structures that may be in proximity to wireless telephone 10, when wireless telephone 10 is not firmly pressed to ear 5. While the illustrated wireless telephone 10 includes a two microphone ANC system with a third near speech microphone NS, some aspects of the present invention may be practiced in a system that does not include separate error and reference microphones, or a wireless telephone that uses near speech microphone NS to perform the function of the reference microphone R. Also, in personal audio devices designed only for audio playback, near speech microphone NS will generally not be included, and the near-speech signal paths in the circuits described in further detail below can be omitted, without changing the scope of the invention, other than to limit the options provided for input to the microphone covering detection schemes.

Figure 2:
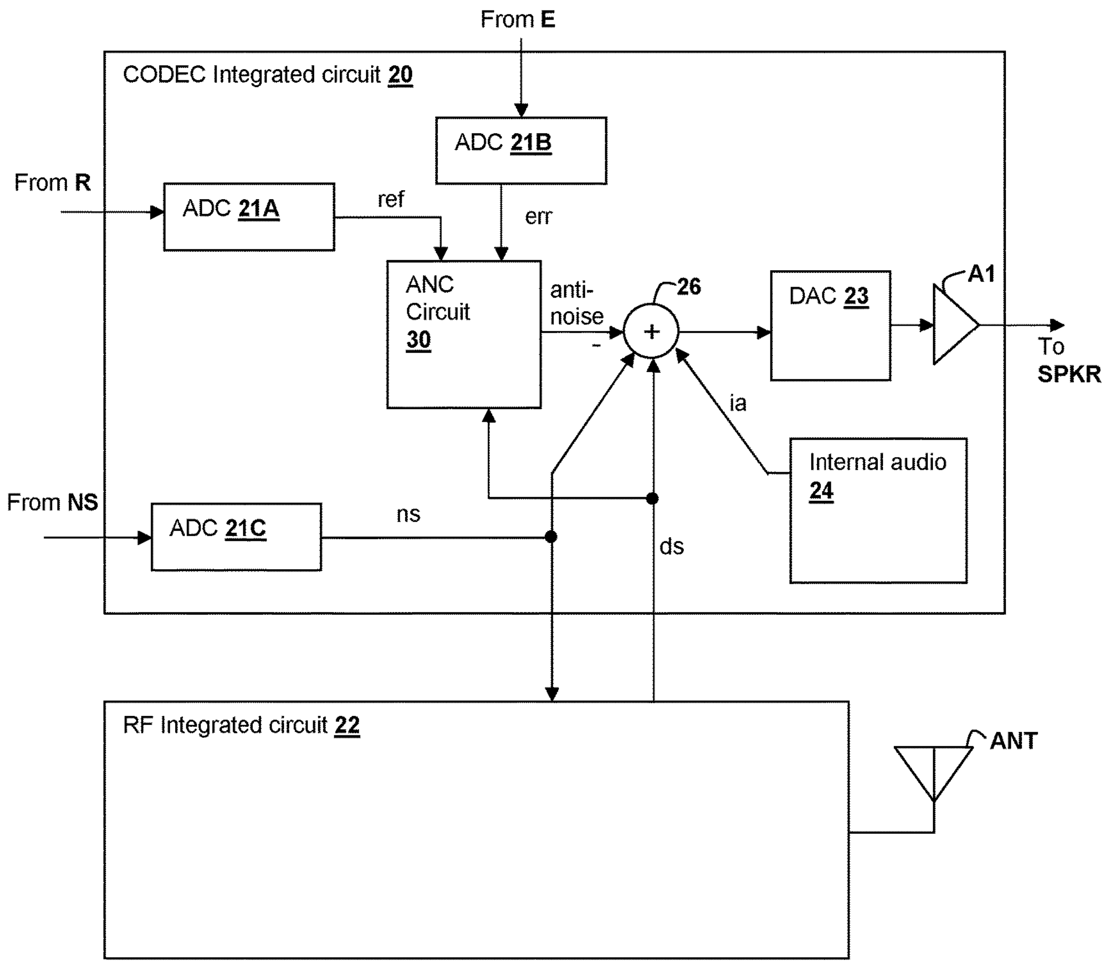
FIG. 2 is a block diagram of circuits within wireless telephone 10 in accordance with an embodiment of the present invention.

Referring now to FIG. 2, circuits within wireless telephone 10 are shown in a block diagram. CODEC integrated circuit 20 includes an analog-to-digital converter (ADC) 21A for receiving the reference microphone signal and generating a digital representation ref of the reference microphone signal, an ADC 21B for receiving the error microphone signal and generating a digital representation err of the error microphone signal, and an ADC 21C for receiving the near speech microphone signal and generating a digital representation ns of the error microphone signal. CODEC IC 20 generates an output for driving speaker SPKR from an amplifier A1, which amplifies the output of a digital-to-analog converter (DAC) 23 that receives the output of a combiner 26. Combiner 26 combines audio signals from internal audio sources 24, the anti-noise signal generated by ANC circuit 30, which by convention has the same polarity as the noise in reference microphone signal ref and is therefore subtracted by combiner 26, a portion of near speech signal ns so that the user of wireless telephone 10 hears their own voice in proper relation to downlink speech ds, which is received from radio frequency (RF) integrated circuit 22 and is also combined by combiner 26. Near speech signal ns is also provided to RF integrated circuit 22 and is transmitted as uplink speech to the service provider via antenna ANT.

Figure 3:
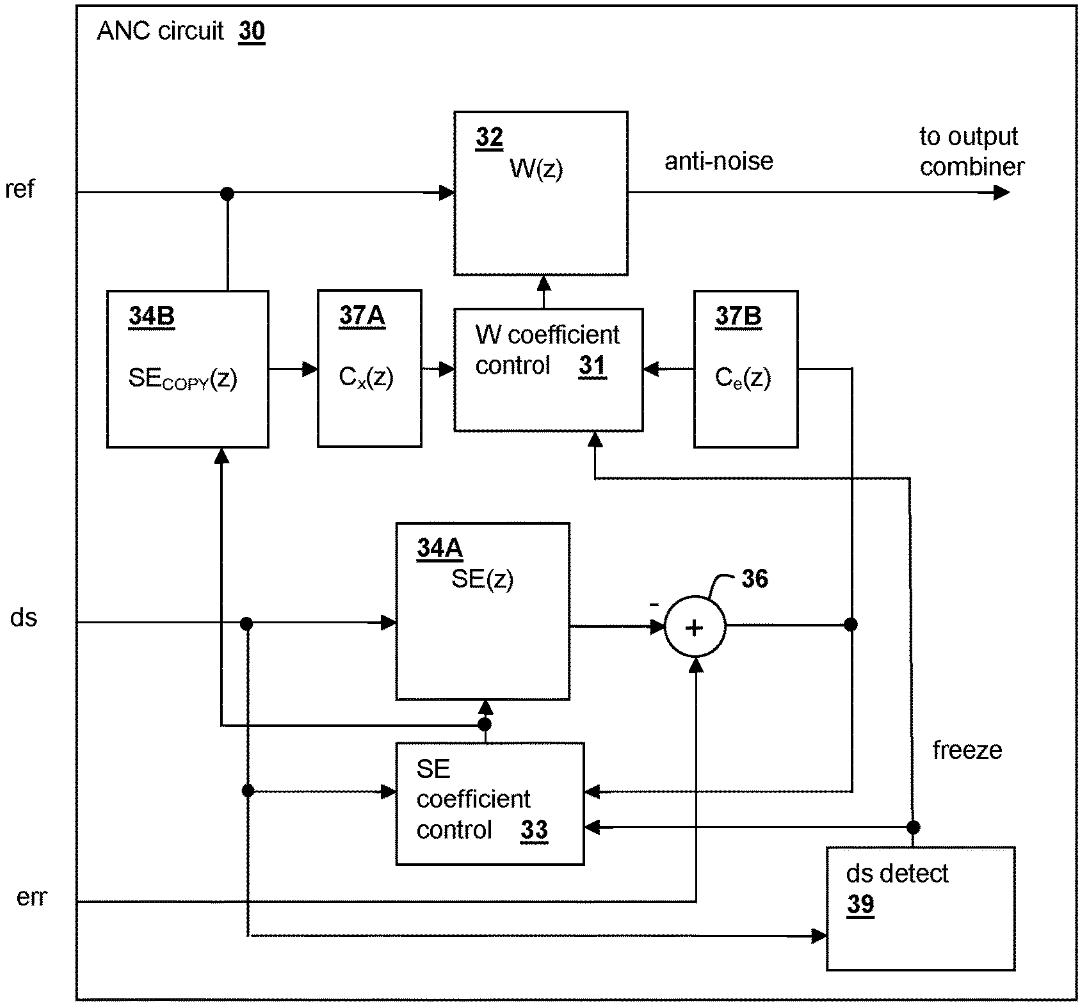
FIG. 3 is a block diagram depicting signal processing circuits and functional blocks within ANC circuit 30 of CODEC integrated circuit 20 of FIG. 2 in accordance with an embodiment of the present invention.

Referring now to FIG. 3, details of ANC circuit 30 are shown in accordance with an embodiment of the present invention. Adaptive filter 32 receives reference microphone signal ref and under ideal circumstances, adapts its transfer function W(z) to be P(z)/S(z) to generate the anti-noise signal, which is provided to an output combiner that combines the anti-noise signal with the audio to be reproduced by the transducer, as exemplified by combiner 26 of FIG. 2. The coefficients of adaptive filter 32 are controlled by a W coefficient control block 31 that uses a correlation of two signals to determine the response of adaptive filter 32, which generally minimizes the error, in a least-mean squares sense, between those components of reference microphone signal ref present in error microphone signal err . The signals compared by W coefficient control block 31 are the reference microphone signal ref as shaped by a copy of an estimate of the response of path S(z) provided by filter 34B and another signal that includes error microphone signal err. By transforming reference microphone signal ref with a copy of the estimate of the response of path S(z), response $SE_{COPY}(z)$, and minimizing the difference between the resultant signal and error microphone signal err, adaptive filter 32 adapts to the desired response of P(z)/S(z). A filter 37A that has a response $C_x(z)$ as explained in further detail below, processes the output of filter 34B and provides the first input to W coefficient control block 31. The second input to W coefficient control block 31 is processed by another filter 37B having a response of $C_e(z)$. Response $C_e(z)$ has a phase response matched to response $C_x(z)$ of filter 37A. Both filters 37A and 37B include a highpass response, so that DC offset and very low frequency variation are prevented from affecting the coefficients of W(z). In addition to error microphone signal err, the signal compared to the output of filter 34B by W coefficient control block 31 includes an inverted amount of downlink audio signal ds that has been processed by filter response SE(z), of which response $SE_{COPY}(z)$ is a copy. By injecting an inverted amount of downlink audio signal ds, adaptive filter 32 is prevented from adapting to the relatively large amount of downlink audio present in error microphone signal err and by transforming that inverted copy of downlink audio signal ds with the estimate of the response of path S(z), the downlink audio that is removed from error microphone signal err before comparison should match the expected version of downlink audio signal ds reproduced at error microphone signal err, since the electrical and acoustical path of S(z) is the path taken by downlink audio signal ds to arrive at error microphone E. Filter 34B is not an adaptive filter, per se, but has an adjustable response that is tuned to match the response of adaptive filter 34A, so that the response of filter 34B tracks the adapting of adaptive filter 34A.

To implement the above, adaptive filter 34A has coefficients controlled by SE coefficient control block 33, which compares downlink audio signal ds and error microphone signal err after removal of the above-described filtered downlink audio signal ds, that has been filtered by adaptive filter 34A to represent the expected downlink audio delivered to error microphone E, and which is removed from the output of adaptive filter 34A by a combiner 36. SE coefficient control block 33 correlates the actual downlink speech signal ds with the components of downlink audio signal ds that are present in error microphone signal err . Adaptive filter 34A is thereby adapted to generate a signal from downlink audio signal ds, that when subtracted from error microphone signal err, contains the content of error microphone signal err that is not due to downlink audio signal ds. A downlink audio detection block 39 determines when downlink audio signal ds contains information, e.g., the level of downlink audio signal ds is greater than a threshold amplitude. If no downlink audio signal ds is present, downlink audio detection block 39 asserts a control signal freeze that causes SE coefficient control block 33 and W coefficient control block 31 to halt adapting.

Figure 4:
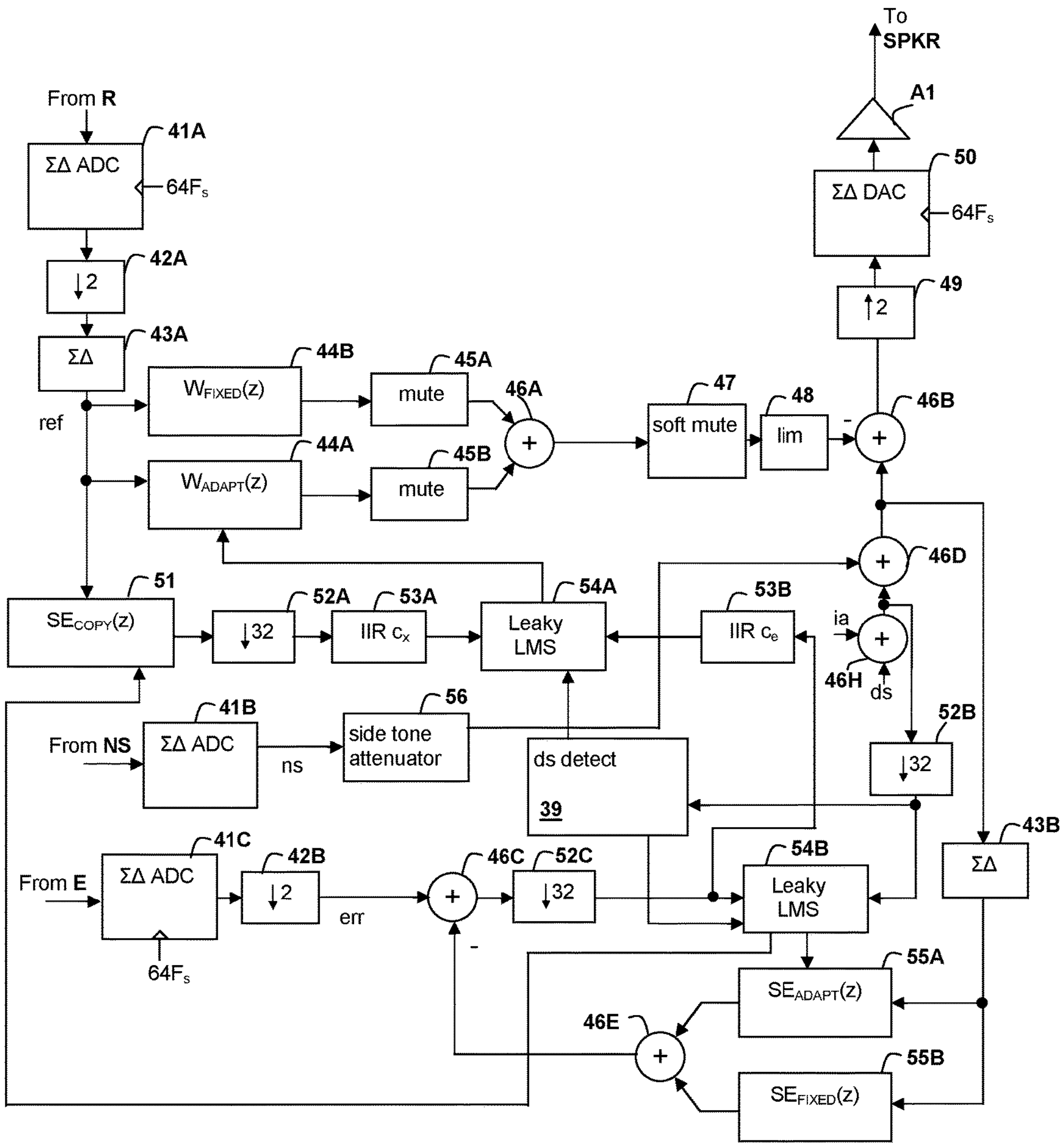
FIG. 4 is a block diagram depicting signal processing circuits and functional blocks within an integrated circuit in accordance with an embodiment of the present invention.

Referring now to FIG. 4, a block diagram of an ANC system is shown for illustrating ANC techniques in accordance with an embodiment of the invention as may be included in the embodiment of the invention depicted in FIG. 3, and as may be implemented within CODEC integrated circuit 20 of FIG. 2. Reference microphone signal ref is generated by a delta-sigma ADC 41A that operates at 64 times oversampling and the output of which is decimated by a factor of two by a decimator 42A to yield a 32 times oversampled signal. A sigma-delta shaper 43A is used to quantize reference microphone signal ref, which reduces the width of subsequent processing stages, e.g., filter stages 44A and 44B. Since filter stages 44A and 44B are operating at an oversampled rate, sigma-delta shaper 43A can shape the resulting quantization noise into frequency bands where the quantization noise will yield no disruption, e.g., outside of the frequency response range of speaker SPKR, or in which other portions of the circuitry will not pass the quantization noise. Filter stage 44B has a fixed response $W_{FIXED}(z)$ that is generally predetermined to provide a starting point at the estimate of P(z)/S(z) for the particular design of wireless telephone 10 for a typical user. An adaptive portion $W_{ADAPT}(z)$ of the response of the estimate of P(z)/S(z) is provided by adaptive filter stage 44A ,which is controlled by a leaky least-means-squared (LMS) coefficient controller 54A. Leaky LMS coefficient controller 54A is leaky in that the response normalizes to flat or otherwise predetermined response over time when no error input is provided to cause leaky LMS coefficient controller 54A to adapt. Providing a leaky controller prevents long-term instabilities that might arise under certain environmental conditions, and in general makes the system more robust against particular sensitivities of the ANC response.

In the system depicted in FIG. 4, reference microphone signal ref is filtered, by a filter 51 that has a response $SE_{COPY}(z)$ that is an estimate of the response of path S(z), the output of which is decimated by a factor of 32 by a decimator 52A to yield a baseband audio signal that is provided, through an infinite impulse response (IIR) filter 53A to leaky LMS 54A. Filter 51 is not an adaptive filter, per se, but has an adjustable response that is tuned to match the combined response of adaptive filters 55A and 55B, so that the response of filter 51 tracks the adapting of response SE(z).The error microphone signal err is generated by a delta-sigma ADC 41C that operates at 64 times oversampling and the output of which is decimated by a factor of two by a decimator 42B to yield a 32 times oversampled signal. As in the system of FIG. 3, an amount of downlink audio ds that has been filtered by an adaptive filter to apply response SE(z) is removed from error microphone signal err by a combiner 46C, the output of which is decimated by a factor of 32 by a decimator 52C to yield a baseband audio signal that is provided, through an infinite impulse response (IIR) filter 53B to leaky LMS 54A. ER filters 53A and 53B each include a high-pass response that prevents DC offset and very low frequency variations from affecting the adaptation of the coefficients of adaptive filter 44A.

Response SE(z) is produced by another parallel set of adaptive filter stages 55A and 55B, one of which, filter stage 55B has fixed response $SE_{FIXED}(z)$, and the other of which, filter stage 55A has an adaptive response $SE_{ADAPT}(z)$ controlled by leaky LMS coefficient controller 54B. The outputs of adaptive filter stages 55A and 55B are combined by a combiner 46E. Similar to the implementation of filter response W(z) described above, response $SE_{FIXED}(z)$ is generally a predetermined response known to provide a suitable starting point under various operating conditions for electrical/acoustical path S(z). Filter 51 is a copy of adaptive filter 55A/55B, but is not itself an adaptive filter, i.e., filter 51 does not separately adapt in response to its own output, and filter 51 can be implemented using a single stage or a dual stage. A separate control value is provided in the system of FIG. 4 to control the response of filter 51, which is shown as a single adaptive filter stage. However, filter 51 could alternatively be implemented using two parallel stages and the same control value used to control adaptive filter stage 55A could then be used to control the adjustable filter portion in the implementation of filter 51. The inputs to leaky LMS control block 54B are also at baseband, provided by decimating a combination of downlink audio signal ds and internal audio ia, generated by a combiner 46H, by a decimator 52B that decimates by a factor of 32, and another input is provided by decimating the output of a combiner 46C that has removed the signal generated from the combined outputs of adaptive filter stage 55A and filter stage 55B that are combined by another combiner 46E. The output of combiner 46C represents error microphone signal err with the components due to downlink audio signal ds removed, which is provided to LMS control block 54B after decimation by decimator 52C. The other input to LMS control block 54B is the baseband signal produced by decimator 52B. The level of downlink audio signal ds (and internal audio signal ia) at the output of decimator 52B is detected by downlink audio detection block 39, which freezes adaptation of LMS control blocks 54A, 54B when downlink audio signal ds and internal audio signal ia are absent.

The above arrangement of baseband and oversampled signaling provides for simplified control and reduced power consumed in the adaptive control blocks, such as leaky LMS controllers 54A and 54B, while providing the tap flexibility afforded by implementing adaptive filter stages 44A-44B, 55A-55B and filter 51 at the oversampled rates. The remainder of the system of FIG. 4 includes combiner 46H that combines downlink audio ds with internal audio ia, the output of which is provided to the input of a combiner 46D that adds a portion of near-end microphone signal ns that has been generated by sigma-delta ADC 41B and filtered by a sidetone attenuator 56 to provide balanced conversation perception. The output of combiner 46D is shaped by a sigma-delta shaper 43B that provides inputs to filter stages 55A and 55B that, in a manner similar to sigma-delta shaper 43A as described above, permits the width of filter stages 55A and 55B to be reduced by quantizing the output of combiner 46D. The quantization noise of sigma-delta shaper 43B is removed by the inherent low-pass response of decimator 52C.

In accordance with an embodiment of the invention, the output of combiner 46D is also combined with the output of adaptive filter stages 44A-44B that have been processed by a control chain that includes a corresponding hard mute block 45A, 45B for each of the filter stages, a combiner 46A that combines the outputs of hard mute blocks 45A, 45B, a soft mute 47 and then a soft limiter 48 to produce the anti-noise signal that is subtracted by a combiner 46B with the source audio output of combiner 46D. The output of combiner 46B is interpolated up by a factor of two by an interpolator 49 and then reproduced by a sigma-delta DAC 50 operated at the 64x oversampling rate. The output of DAC 50 is provided to amplifier A1, which generates the signal delivered to speaker SPKR.

Figure 5:
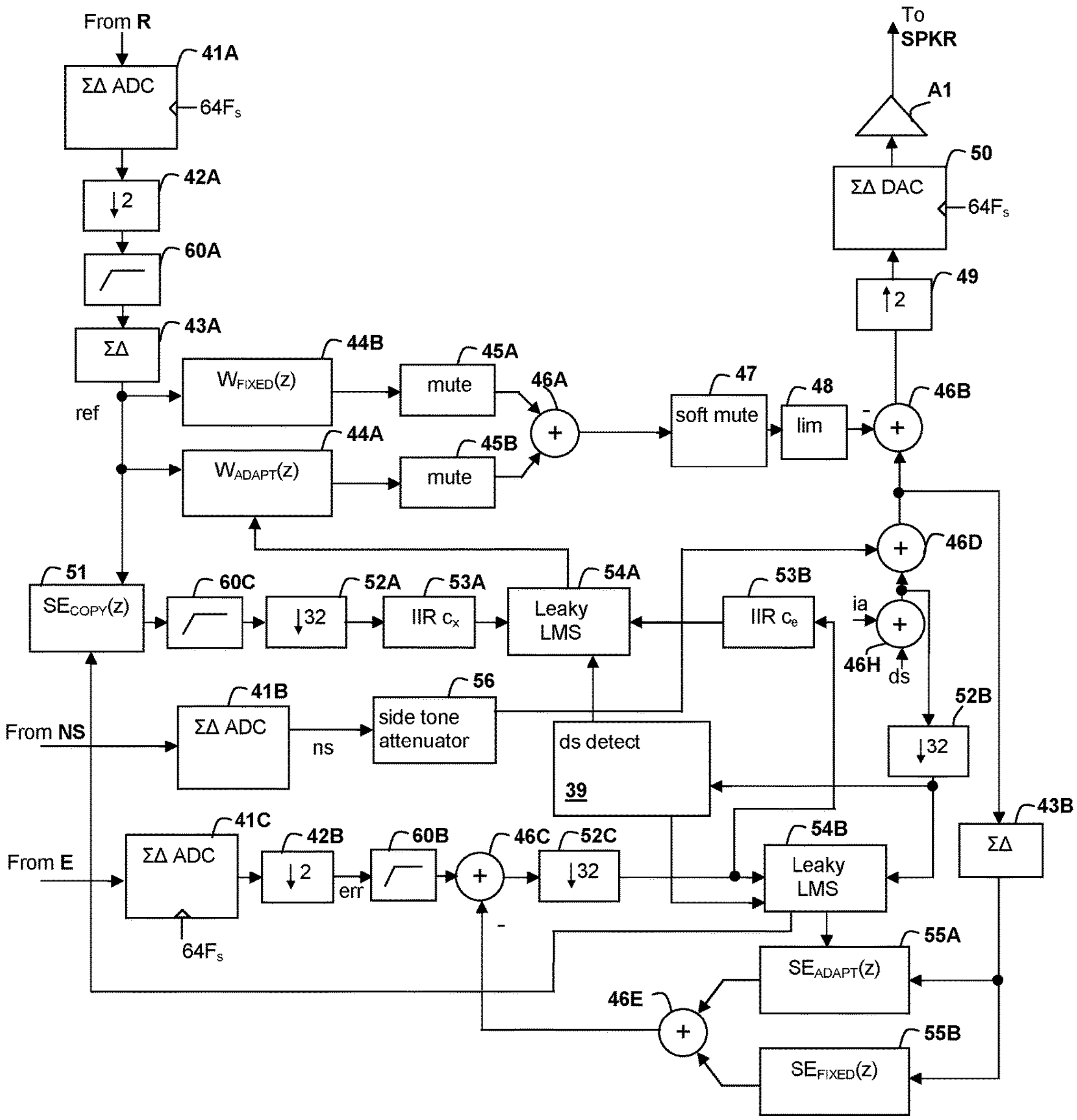
FIG. 5 is a block diagram depicting signal processing circuits and functional blocks within an integrated circuit in accordance with another embodiment of the present invention.

Referring now to FIG. 5, a block diagram of an ANC system is shown for illustrating ANC techniques in accordance with another embodiment of the invention that may be included in the embodiment of the invention depicted in FIG. 3, and as may be implemented within CODEC integrated circuit 20 of FIG. 2. The ANC system of FIG. 5 is similar to that of FIG. 4, so only differences between them will be described in detail below. Rather than providing a high-pass response at the inputs to leaky LMS 54A, DC components are removed directly from reference microphone signal ref and error microphone signal err by providing respective high-pass filters 60A and 60B in the reference and error microphone signal paths. An additional high-pass filter 60C is then included in the SE copy signal path after filter 51. The architecture illustrated in FIG. 5 is advantageous in that high-pass filter 60A removes DC and low frequency components from the anti-noise signal path and that otherwise would be passed by filter stages 44A, 44B in the anti-noise signal provided to speaker SPKR, wasting energy, generating heat and consuming dynamic range. However, since reference microphone signal ref needs to contain some low-frequency information in frequency bands that can be canceled by the ANC system, i.e., in frequency ranges for which speaker SPKR has significant response, filter 60A is designed to pass such frequencies, while for optimum adaptation of leaky LMS 54A, a higher high-pass cut-in frequency, e.g., 200 Hz is employed. The phase response of filters 60B and 60C is matched to maintain a stable operating condition for leaky LMS 54A.

Each or some of the elements in the systems of FIG. 4 and FIG. 5, as well in as the exemplary circuits of FIG. 2 and FIG. 3, can be implemented directly in logic, or by a processor such as a digital signal processing (DSP) core executing program instructions that perform operations such as the adaptive filtering and LMS coefficient computations. While the DAC and ADC stages are generally implemented with dedicated mixed-signal circuits, the architecture of the ANC system of the present invention will generally lend itself to a hybrid approach in which logic may be, for example, used in the highly oversampled sections of the design, while program code or microcode-driven processing elements are chosen for the more complex, but lower rate operations such as computing the taps for the adaptive filters and/or responding to detected events such as those described herein.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A personal audio device, comprising:

a personal audio device housing;

a transducer mounted on the housing for reproducing an audio signal including both source audio for playback to a listener and an anti-noise signal for countering the effects of ambient audio sounds in an acoustic output of the transducer;

at least one microphone mounted on the housing in proximity to the transducer for providing at least one microphone signal indicative of the acoustic output of the transducer and the ambient audio sounds at the transducer;

a processing circuit that implements an adaptive filter having a response that generates the anti-noise signal to reduce the presence of the ambient audio sounds heard by the listener, wherein the processing circuit implements a coefficient control block that shapes the response of the adaptive filter in conformity with the at least one microphone signal by adapting the response of the adaptive filter to minimize a component of the at least one microphone signal due to the ambient audio sounds, wherein the processing circuit further implements a first filter having a first frequency response that filters the at least one microphone signal to provide an input to the adaptive filter from which the anti-noise signal is generated, and wherein the processing circuit further implements a second filter having a second frequency response that differs from the first frequency response, wherein the second filter filters the at least one microphone signal to provide a first input to the coefficient control block.

2. The personal audio device of claim 1, wherein the at least one microphone comprises:

an error microphone that provides an error microphone signal indicative of the acoustic output of the transducer and the ambient audio sounds at the transducer; and a reference microphone that provides a reference microphone that provides a reference microphone signal indicative of the ambient audio sounds, wherein the first filter filters the reference microphone signal to provide the input to the adaptive filter, wherein the coefficient control block receives the reference microphone signal filtered by the second filter as the first input to the coefficient control block.

3. The personal audio device of claim 2, wherein the processing circuit further implements a third filter having a third frequency response that filters the error microphone signal to provide a filtered error microphone signal to a second input of the coefficient control block.

4. The personal audio device of claim 1, wherein the first frequency response has a cut-in frequency of approximately 200 Hz and wherein the second frequency response has a cut-in frequency substantially below 200 Hz in frequency bands in which the transducer has significant response.

5. The personal audio device of claim 1, wherein the first filter and the second filter are high-pass filters.

6. The personal audio device of claim 1, wherein the first filter and the second filter are digital filters.

7. A method of canceling ambient audio sounds in the proximity of a transducer of a personal audio device, the method comprising:

measuring an output of the transducer and the ambient audio sounds at the transducer with at least one microphone;

first filtering the at least one microphone signal with a first filter having a first frequency response to generate a first filtered microphone signal;

second filtering the at least one microphone signal with a second filter having a second frequency response that differs from the first frequency response to generate a second filtered microphone signal; and adaptively generating an anti-noise signal for countering the effects of ambient audio sounds at an acoustic output of the transducer by adapting a response of an adaptive filter that filters the first filtered microphone signal by adjusting coefficients of the adaptive filter with a coefficient control that receives the second filtered microphone signal as an input.

8. The method of claim 7, wherein the at least one microphone comprises an error microphone that provides an error microphone signal indicative of the acoustic output of the transducer and the ambient audio sounds at the transducer and a reference microphone that provides a reference microphone that provides a reference microphone signal indicative of the ambient audio sounds, wherein the first filtering filters the reference microphone signal to provide the input to the adaptive filter, wherein the coefficient control block receives the reference microphone signal filtered by the second filtering as the first input to the coefficient control block.

9. The method of claim 7, further comprising third filtering the error microphone signal with a third filter having a third frequency response, wherein the coefficient control block receives the error microphone signal filtered by the third filtering as a second input to the coefficient control block.

10. The method of claim 7, wherein the first frequency response has a cut-in frequency of approximately 200 Hz and wherein the second frequency response has a cut-in frequency substantially below 200 Hz in frequency bands in which the transducer has significant response.

11. The method of claim 7, wherein the first filter and the second filter are high-pass filters.

12. The method of claim 7, wherein the first filter and the second filter are digital filters.

13. An integrated circuit for implementing at least a portion of a personal audio device, comprising:

an output for providing a signal to a transducer including both source audio for playback to a listener and an anti-noise signal for countering the effects of ambient audio sounds in an acoustic output of the transducer;

at least one microphone input for receiving at least one microphone signal indicative of the acoustic output of the transducer and the ambient audio sounds at the transducer; and a processing circuit that implements an adaptive filter having a response that generates the anti-noise signal to reduce the presence of the ambient audio sounds heard by the listener, wherein the processing circuit implements a coefficient control block that shapes the response of the adaptive filter in conformity with the microphone signal by adapting the response of the adaptive filter to minimize a component of the microphone signal due to the ambient audio sounds, wherein the processing circuit further implements a first filter having a first frequency response that filters the microphone signal to provide an input to the adaptive filter from which the anti-noise signal is generated, and wherein the processing circuit further implements a second filter having a second frequency response that differs from the first frequency response, wherein the second filter filters the microphone signal to provide a first input to the coefficient control block.

14. The integrated circuit of claim 13, wherein the at least one microphone input comprises:

an error microphone input that receives an error microphone signal indicative of the acoustic output of the transducer and the ambient audio sounds at the transducer; and a reference microphone input that receives a reference microphone signal indicative of the ambient audio sounds, wherein the first filter filters the reference microphone signal to provide the input to the adaptive filter, wherein the coefficient control block receives the reference microphone signal filtered by the second filter as the first input to the coefficient control block.

15. The integrated circuit of claim 14, wherein the processing circuit further implements a third filter having a third frequency response that filters the error microphone signal to provide a filtered error microphone signal to a second input of the coefficient control block.

16. The integrated circuit of claim 13, wherein the first frequency response has a cut-in frequency of approximately 200 Hz and wherein the second frequency response has a cut-in frequency substantially below 200 Hz in frequency bands in which the transducer has significant response.

17. The integrated circuit of claim 13, wherein the first filter and the second filter are high-pass filters.

18. The integrated circuit of claim 13, wherein the first filter and the second filter are digital filters.

* * * * *